(12) United States Patent
Nomura

(10) Patent No.: US 9,267,897 B2
(45) Date of Patent: Feb. 23, 2016

(54) OPTICAL SENSOR ELEMENT FOR ANALYTE ASSAY IN A BIOLOGICAL FLUID, AND METHOD OF MANUFACTURE THEREOF

(71) Applicant: Light Pointe Medical, Inc., St. Louis Park, MN (US)

(72) Inventor: Hiroshi Nomura, Shorewood, MN (US)

(73) Assignee: Light Pointe Medical, Inc., St. Louis Park, MN (US)

( * ) Notice: Subject to any disclaimer, the term of this patent is extended or adjusted under 35 U.S.C. 154(b) by 42 days.

(21) Appl. No.: 14/057,868

(22) Filed: Oct. 18, 2013

(65) Prior Publication Data

US 2015/0110676 A1  Apr. 23, 2015

(51) Int. Cl.
| | | |
|---|---|---|
| *G01N 21/65* | (2006.01) | |
| *G01N 21/75* | (2006.01) | |
| *G01N 21/77* | (2006.01) | |
| *G02B 6/02* | (2006.01) | |
| *G02B 1/04* | (2006.01) | |
| *G02B 1/12* | (2006.01) | |

(52) U.S. Cl.
CPC ............ *G01N 21/7703* (2013.01); *G02B 1/048* (2013.01); *G02B 1/12* (2013.01); *G02B 6/023* (2013.01); *G01N 2021/772* (2013.01)

(58) Field of Classification Search
CPC .......... G01N 21/6428; G01N 21/7703; G01N 2021/772; G01N 2021/6434
USPC ............................................. 422/82.06, 82.11
See application file for complete search history.

(56) References Cited

U.S. PATENT DOCUMENTS

| | | | |
|---|---|---|---|
| 5,560,781 A | 10/1996 | Banks et al. | |
| 5,656,241 A * | 8/1997 | Seifert et al. | ............... 422/82.06 |
| 5,859,937 A | 1/1999 | Nomura | |
| 8,008,068 B2 | 8/2011 | Nomura | |
| 2005/0123451 A1* | 6/2005 | Nomura | ..................... 422/82.11 |
| 2008/0240652 A1* | 10/2008 | Todori et al. | ................... 385/27 |
| 2009/0219509 A1 | 9/2009 | Nomura | |
| 2011/0097755 A1* | 4/2011 | Nomura | ......................... 435/14 |

OTHER PUBLICATIONS

Banks, Bruce A. et al. Atomic Oxygen Textured Polymers, NASA Technical Memorandum 106769, Prepared for the 1995 Spring Meeting sponsored by the Materials Research Society, San Francisco, CA, Apr. 17-21, 1995. 22 Pages.

\* cited by examiner

*Primary Examiner* — Paul Hyun
(74) *Attorney, Agent, or Firm* — David H. Carroll

(57) ABSTRACT

Beginning with a sheet of optically transparent material, one may fabricate a great many shaped optical wafers, each in the form of a thin and essentially flat piece of optical material having a narrow cross-sectional width relative to length, and a sharply narrowed tip at one end. The fabrication process involves passing a sheet of optically transparent material through one or more operational steps wherein cutting, shearing, embossing, microperforating, or a combination thereof is performed. The fabrication process may further include a cladding operation, a tip texturing operation, and an analyte-reactive reagent deposition operation. The completed optical wafers are separated and each may be mounted into a user-operated device along with systems for educing a fluid sample to be expressed from a living organism, for bringing the tip of the optical wafer into contact with the fluid sample, and for illuminating and assaying the fluid sample.

4 Claims, 6 Drawing Sheets

OPTICAL SENSOR ELEMENT FOR ANALYTE ASSAY IN A BIOLOGICAL FLUID, AND METHOD OF MANUFACTURE THEREOF

BACKGROUND OF THE INVENTION

1. Field of the Invention

The present invention relates to sensing analyte concentration in a biological fluid, and more particularly to an optical sensor element for measuring analyte concentration in a biological fluid by optical means and a method of manufacture thereof.

2. Description of Related Art

Optical sensors using waveguides such as optical fibers are very useful in performing analyte assays in biological fluids. U.S. Pat. No. 5,859,937 issued Jan. 12, 1999 to Nomura, for example, describes a minimally invasive medical testing device and method for its use which utilizes a light-conducting optical fiber sensor element having a localized textured site thereon, wherein a reagent is deposited. Interaction of the reagent with an analyte specific to the reagent produces a response, such as development of a colored product, which is detectable by means of a change in characteristics of a light beam transmittable through the optical fiber. By means of the textured site and its increased surface area, the sensitivity of the medical testing device is greatly enhanced. The sensor is particularly useful in blood glucose determinations, requiring smaller blood samples than flat strip devices. Improvements in such optical fiber sensor elements have even further increased their sensitivity. Examples of such improved optical fiber sensor elements may be found in, for example, United States Published Patent Application No. 2009/0219509 published Sep. 3, 2009 in the name of Nomura, United States Published Patent Application No. 2011/0097755 published Apr. 28, 2011 in the name of Nomura, and U.S. Pat. No. 8,008,068 issued Aug. 30, 2011 to Nomura.

The handling of individual optic fibers during manufacture is not without difficulty in a practical industrial process. Steps would normally include cutting optic fibers into short lengths, attaching them to some form of belt or carrier, exposing a belted bundle or continuous array of optic fiber ends to an etchant such as a stream of atomic oxygen gas, then depositing a mixture of analyte-reactive reagent and hollow polymeric particles on the treated tips, followed by drying and repositioning of such treated fibers into cartridges for use by a consumer such as a diabetic patient. Improvements in optical sensor elements to enhance their manufacturability and improvements in the methods of manufacture thereof are desirable.

BRIEF SUMMARY OF THE INVENTION

One embodiment of the present invention is an optical sensor element for determination of an analyte in a biological fluid, comprising a flat optical waveguide elongated in a longitudinal direction and having two parallel major surfaces and an edge contiguous to the major surfaces, a portion of the edge being a tip transverse to the longitudinal direction, a further portion of the edge being a base transverse to the longitudinal direction, and further portions of the edge being two sides extending between the base and the tip generally in the longitudinal direction. The tip is textured, the major surfaces are coated with cladding; and each of the sides is partially coated with cladding toward the base and being fully coated with cladding toward the tip. The optical sensor element further comprises an analyte-reactive reagent disposed on the tip.

Another embodiment of the preset invention is an optical wafer for use in manufacturing an optical sensor element, comprising a flat optically transparent body elongated in a longitudinal direction and tapering down at one end to a tip, the tip being transverse to the longitudinal direction and presenting a textured field of elongated projections; and an analyte-reactive reagent disposed on the tip.

Another embodiment of the preset invention is a method of fabricating optical wafers for biological fluid sensors, comprising: establishing a plurality of cutouts in a sheet of optically transparent polymer material to define respective tapered portions of the optical wafers and expose edges thereof; establishing a plurality of transverse lines in the sheet to define respective main portions of the optical wafers and partially expose edges thereof; separating the sheet along a plurality of longitudinal lines into a plurality of strips to expose respective tips of the optical wafers; applying a texturing treatment to the tips exposed in the separating step to form a field of elongated projections in the tips; depositing a fluid slurry mixture of analyte-reactive reagent and light scattering particles within the field of elongated projections; and following the texturing treatment applying step and the fluid slurry mixture depositing step, separating the optical wafers from one another along the transverse lines.

DETAILED DESCRIPTION OF THE INVENTION

Figure 1:
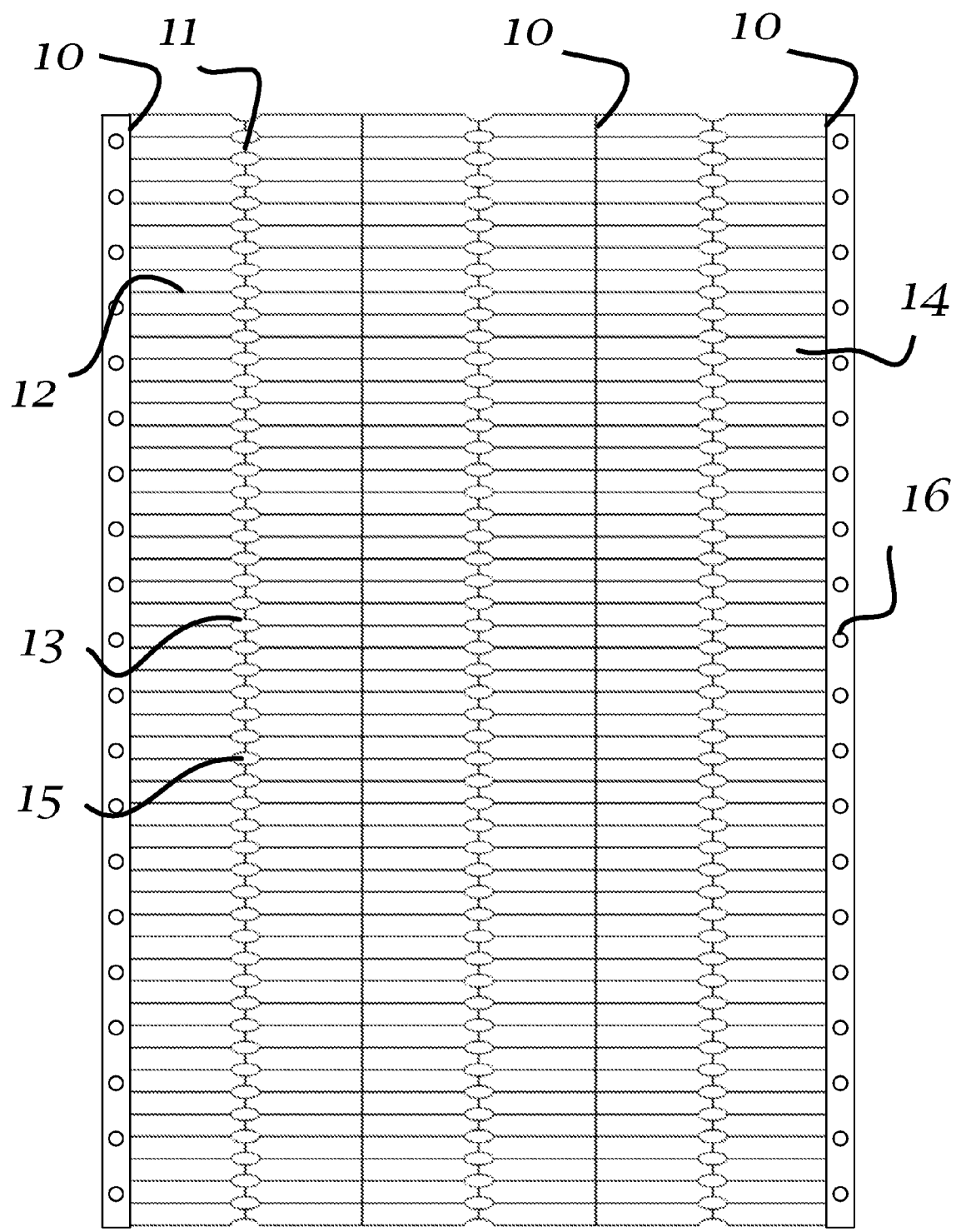
FIG. 1 is a pattern drawing of a sheet of optical material having lines of separation therein for defining optical wafers.

Various optical fiber sensor elements are described in U.S. Pat. No. 5,859,937 issued Jan. 12, 1999 to Nomura, United States Published Patent Application No. 2009/0219509 published Sep. 3, 2009 in the name of Nomura, United States Published Patent Application No. 2011/0097755 published Apr. 28, 2011 in the name of Nomura, and U.S. Pat. No. 8,008,068 issued Aug. 30, 2011 to Nomura, all of which are incorporated herein in their entirety by reference thereto, and collectively referred to herein as the Nomura patent documents. Some of the optical sensor elements described herein possess many of the analytical advantages of these earlier optical fiber sensor elements, including a one-step testing process for analyte measurement, analyses of analytes in very small sample volumes in contact with a very small tip (a blood sample size of only around 0.1 microliter in diabetes blood glucose testing, for example), rapid test results of two seconds or less, and elimination of hemoglobin interference. However, in addition, such optical sensor elements are also suitable for manufacture by highly efficient and cost-effective methods which avoid some of the manufacturing and handling disadvantages that arise in the manipulation of short lengths of optical fibers, and substantially reduce manufacturing costs.

At least one of the implementations described herein may start with a sheet of optically transparent material, and derives therefrom a shaped optical wafer in the form of a thin and preferably flat piece of optical material having a narrow cross-sectional width relative to length, and further having a sharply narrowed tip at one end of the length of the shaped body, this tip approximating the same cross-sectional distal area as the distal tip of a comparable optic fiber as described in the previously-referenced Nomura patent documents. To form the optical wafers, the sheet of optically transparent material is passed through one or more operational steps wherein cutting (including scoring), shearing, embossing, micro-perforating, or any combination of cutting/shearing/embossing/micro-perforating/of the material is performed. Where scoring or embossing is used, to form lines, the lines may be formed on only one side of the sheet, or may be formed on both sides in registration with one another. The purpose of these operational steps is to prepare an elongated optical body, which may be referred to as an optical wafer, having in general the optical sensing characteristics of an optical fiber sensor but being of a different shape than a fiber so as to facilitate manufacture and post-manufacture handling. At least one of the implementations may further include sufficient cladding of the elongated optical body, texturing of a distal tip of the elongated optical body, and the modification of the textured tip with an analyte-reactive reagent composition that provides, for instance, a colorimetric change when contacted with a fluid containing the associative analyte. At least one of the implementations may further include a user-operated device containing the elongated optical body, any suitable mechanism for bringing the tip of the elongated optical body into contact with a fluid sample to be tested, and any suitable optical system for coupling light to and from the optical body (such as a lens, grating coupler, or prism coupler) via its base in order to illuminate the tip and to assay light reflectance received by the tip for correlative assay of an analyte. At least one of the implementations may further include any suitable mechanism for educing a fluid sample to be expressed from a living organism, such as by a lancet.

Figure 3:
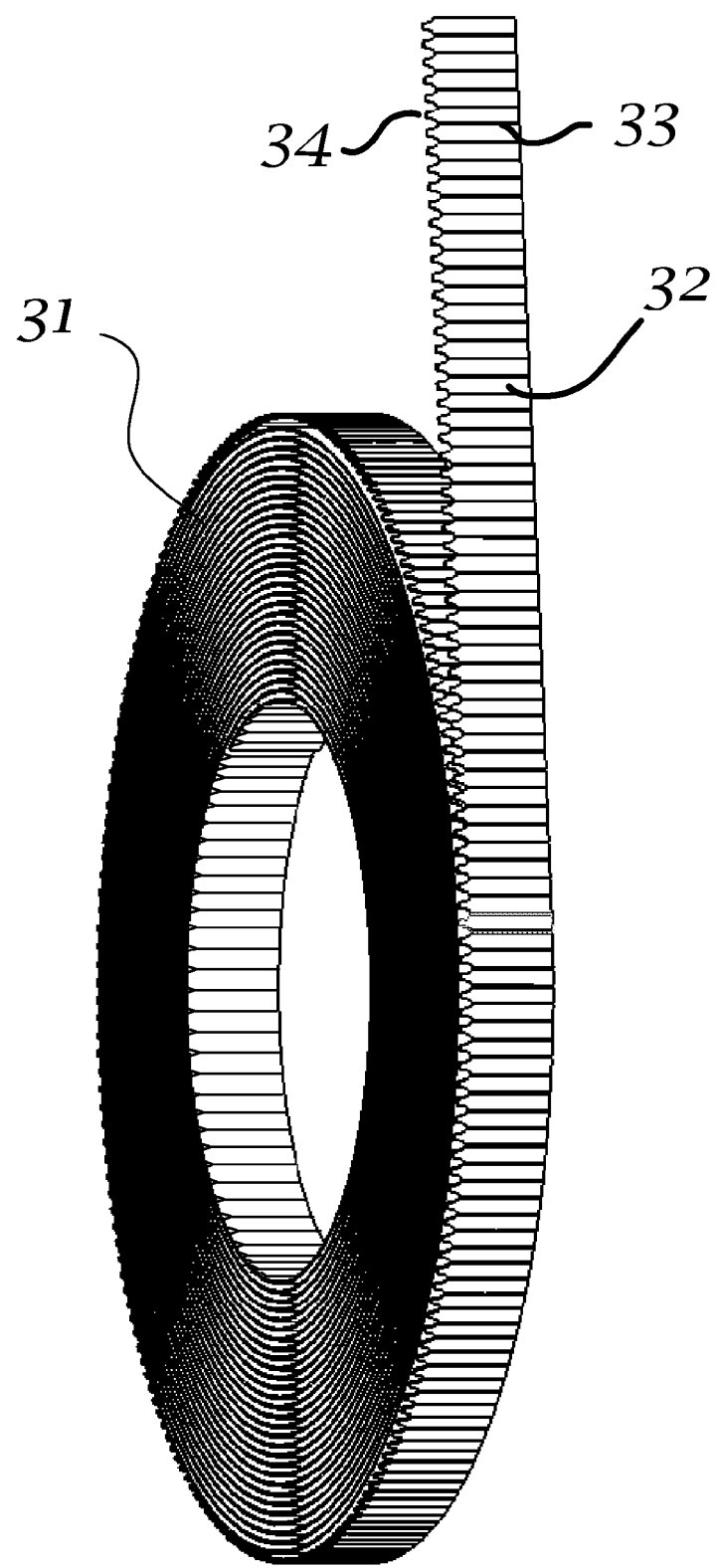
FIG. 3 is a 3-dimensional drawing of a strip of optical wafers of FIG. 2 as rolled into a roll of optical wafers connected along their sides and having projecting tips.
Figure 4:
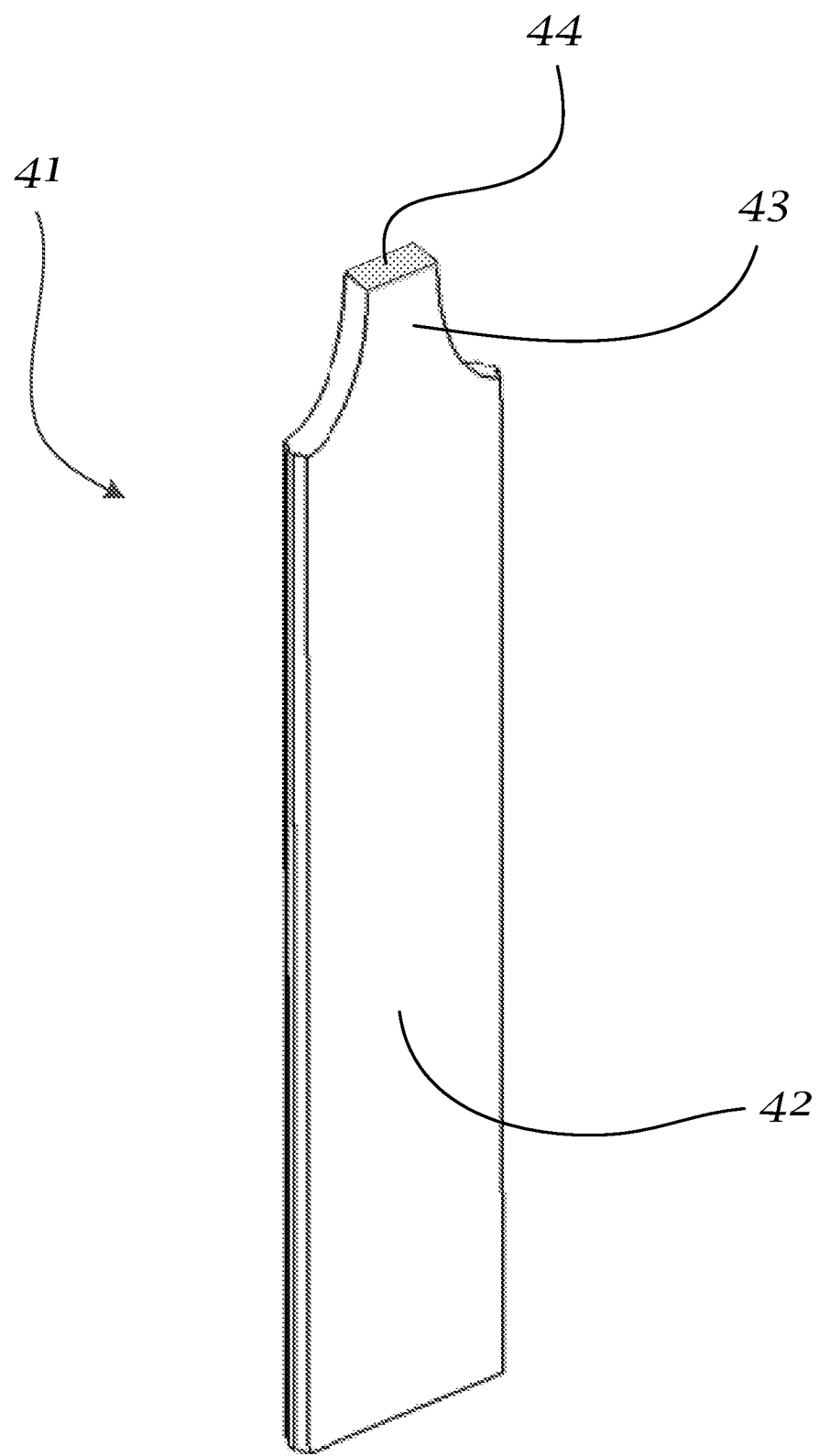
FIG. 4 is a 3-dimensional drawing of an individual optical wafer of the type shown in FIGS. 1, 2 and 3.
Figure 5:
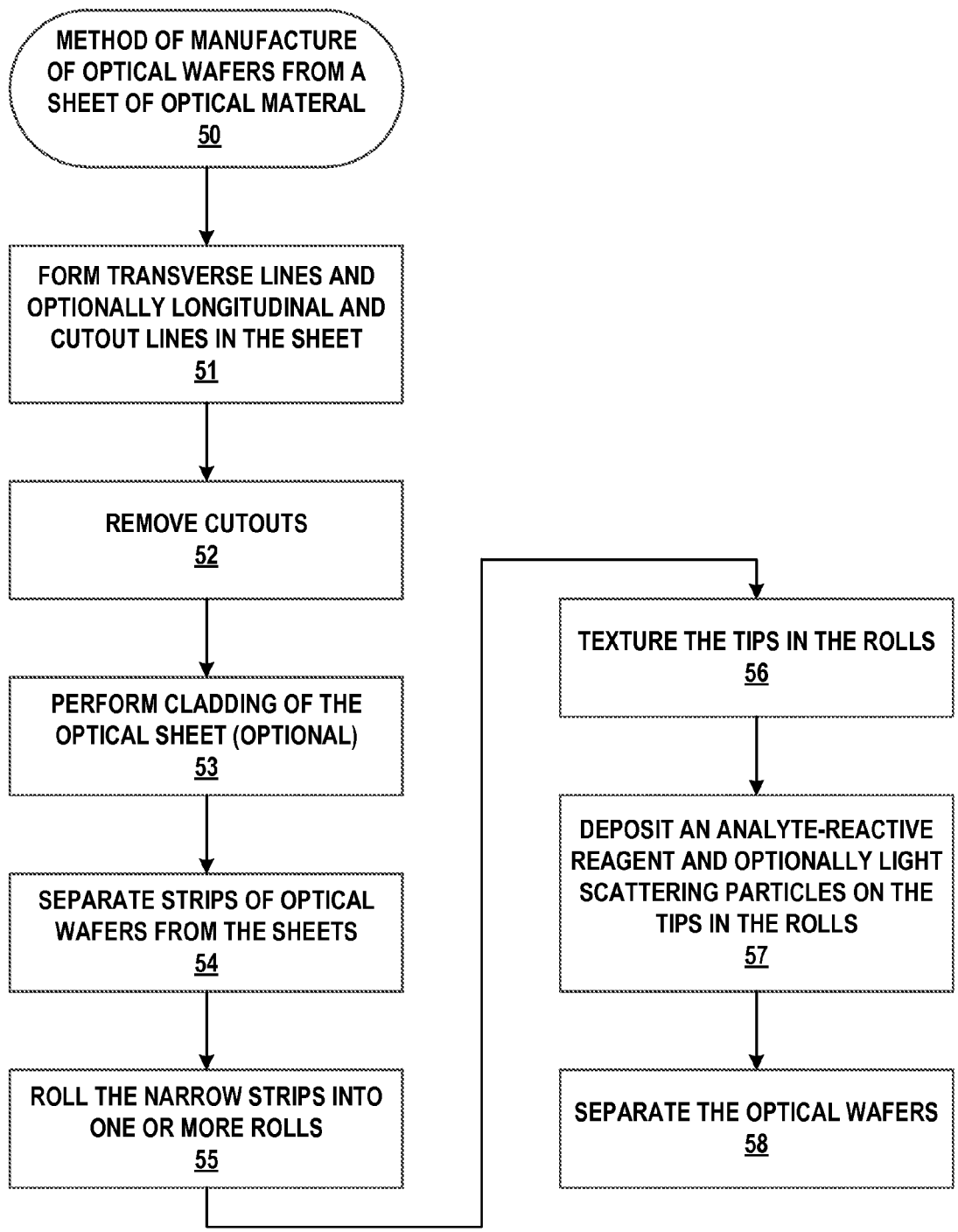
FIG. 5 is a flowchart of a method of manufacture of optical wafers.

FIGS. 1 through 4 show the results of various steps of an illustrative manufacturing process shown in the flowchart of FIG. 5.

FIG. 1 shows an exemplary implementation of a suitable pattern that may be formed in a sheet or in continuous sheeting of optically transparent material that lead to individual optical wafers when complete. Shown in FIG. 1 is a sheet or a section of a continuous sheeting that contains embossed or cut longitudinal lines 10 and 11 in the machine direction, embossed or cut transverse lines 12 in the transverse direction, and oval embossed or cut cutout lines 13. These lines may be formed at the same time as shown in block 51 of the illustrative manufacturing process 50 shown in FIG. 5, or may be formed at different times. Illustratively, the cutout lines 13 and the transverse lines 12 may be formed together first, and the longitudinal lines 10 and 11 may be formed later in the manufacturing process. Alternatively, the cutout lines 13 may be formed and the cutouts 15 removed (for example, punched out) before the transverse lines 12 are formed. If the cutouts are both defined and removed using punches having shaped cutting edges, the cutout lines 13 are not needed. Guide holes 16 may be provided to assist in operations requiring high precision, such as punching, embossing, and cutting.

The cutouts 15 provide for the narrowing of a portion of the outlined optical wafers 14. Other shapes such as circular, diamond, rectangle, triangular, and so forth may alternatively be used for the cutouts 15, and the selection of a specific shape may be influenced by such design considerations as the optical performance of the light guide which is formed from the optical wafer, and handling considerations during manufacture. From a manufacturing perspective, circular and oval shaped cutouts 15 may be preferable to avoid stress regions during manufacture, in that no sharp corners or recesses are present that would interfere with punching out of the cutouts 15. All embossed or cut lines need not be formed in a single process step. In one implementation, for example, separation of portions of the sheet material involves sequential operations. Note that the orientation of transverse versus machine-direction lines may be varied or transposed, particularly if the starting material consists of single sheets of optical material. However, when starting with continuous sheeting as with a long roll of optical material sheeting, the arrangement of lines and their orientation as illustrated in FIG. 1 is particularly advantageous.

As shown in blocks 51 and 52 of FIG. 5, transverse lines 12 and optionally cutout lines 13 and longitudinal lines 10 and 11 may be formed in the sheet of optical material (block 51), and the cutouts 15 may be removed from the sheet of optical material by punching them out. The organization of blocks 51 and 52 is not to be understood to require a particular order, and the process steps may be performed in various ways and in a different order. In one illustrative implementation, all embossed or cut lines including the cutout lines 13 may be formed together, and the cutouts 15 subsequently punched out. In another illustrative implementation, the cutouts may be punched out using a suitable cutting punch without forming any cutout lines 13, followed by formation of the transverse lines 12, and followed later in the manufacturing process by formation of the longitudinal lines 10 and 11. Any suitable technique such as embossing, microperforating, or partial cutting of the optical material may be used to form the longitudinal lines 10 and 11, the transverse lines 12, and the cutout lines 13.

Light guides use cladding on their optical material to confine the light and to minimize loss of light through the outer walls. Although cladding of the optical sheeting may be employed before or after the embossing or cutting steps, it is advantageous to perform the cladding operation after the cutouts 15 are removed and the transverse lines 12 are formed in the sheet of optical material, so that the tapered sidewalls of the optical wafer flanking the tip are cladded, and so that the main sidewalls of the optical wafer as defined by the transverse lines 12 are at least partially cladded, to improve optical performance. While the longitudinal lines 10 and 11 may be formed prior to the cladding operation, some implementations may benefit from forming either or both of the longitudinal lines 10 and 11 after the cladding operation, so that the tips, bases or both of the separated optical wafers are free of any cladding. Cladding may be performed by dip-coating, spraying, roller-coating, or similar such methods. A particularly suitable cladding technique is deposit of a cladding material by plasma polymerization. Plasma polymerization provides for pinhole-free coatings and also achieves penetration into embossed or microperforated recesses. Effective cladding compounds typically have an index of refraction that is significant different than the refractive index of the optical material being coated. Fluorocarbon-containing coatings are particularly advantageous. Fluorocarbon coatings may be formed through plasma polymerization of fluorine-containing monomers such as tetrafluoroethylene, hexafluorobenzene, or hexafluoropropene. Chemical cladding is not necessarily required. In some applications, so-called "air-cladding" may suffice, in that the index of refraction of air differs sufficiently from that of a polymeric material serving as optical wave guide. Air-cladding is generally suitable when the surface of the optical wafer (other than the analyte-reactive sensor zone) is not likely to be in contact with water or water-based fluid and remains dry. While the cladding operation (block 53) is therefore optional, it may be quite advantageous in many applications.

The optical wafers themselves may be formed from any of many suitable optically transparent compositions. Suitable choices include polymeric compounds such as celluloids, cellulose acetates, polyesters, polystyrenes, polymethacrylates, polyolefins, halogen-containing polyolefins, polysulfones, polycarbonates, and copolymers or terpolymers of these different compositions. Other suitable choices include cellulose acetates, polycarbonates, methyl methacrylate polymer and copolymers, polystyrene, and styrene-acrylonitrile copolymer. Continuous sheeting of many of these compositions is available and amenable to being processed through die-cut roller machines. Alternatively, sheets may be handled and processed by means of various types of cutting and embossing equipment. Processing may be done at room temperature or at elevated temperatures. For sheeting where rigidity of the polymer composition may present processing difficulty, elevated temperatures sufficient to soften the polymer composition may be employed.

Figure 2:
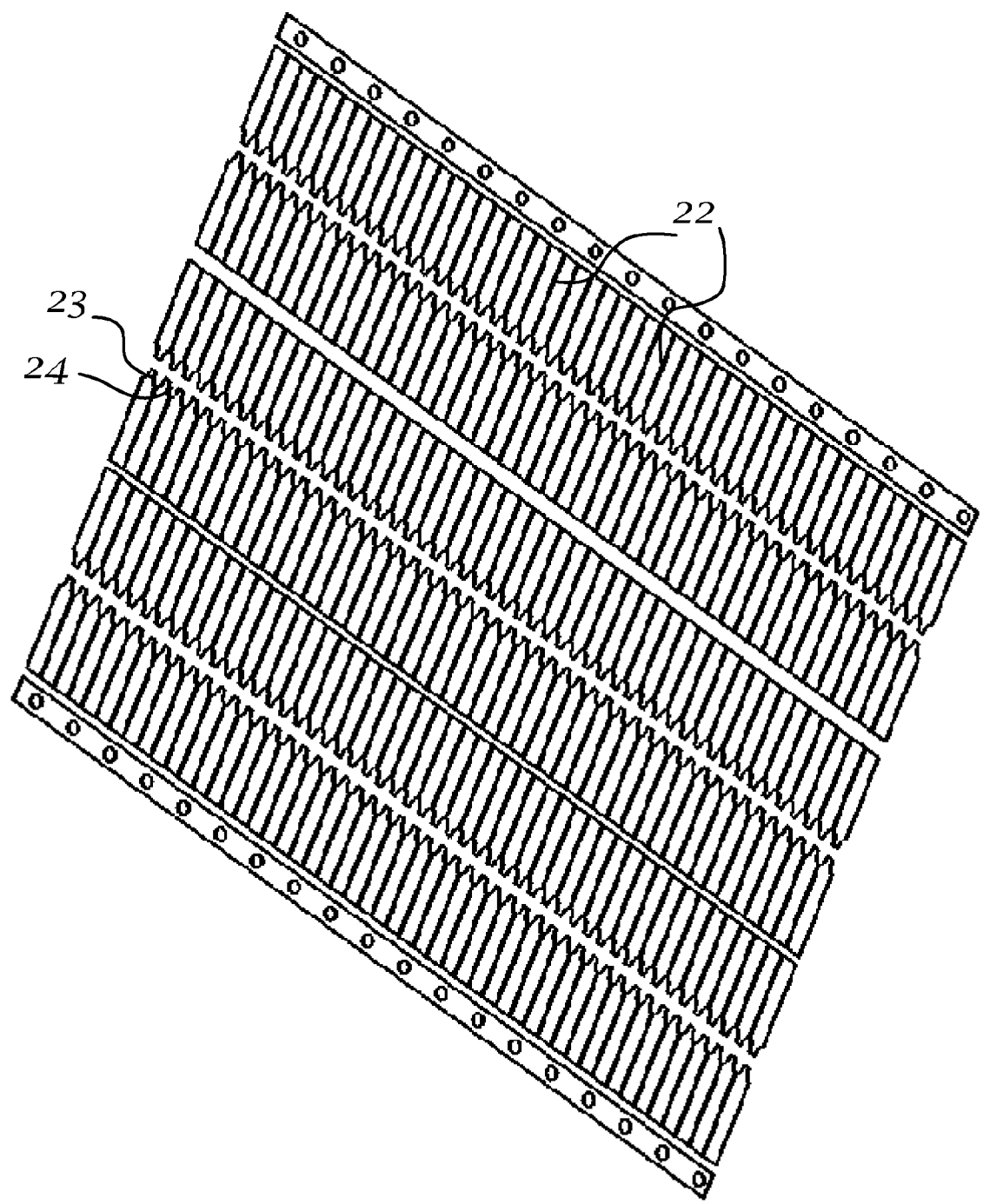
FIG. 2 is a perspective drawing showing a partial separation of sections of the optical material of FIG. 1 into strips of optical wafers.

Following the embossing or die-cutting operations, partial separation of the sheeting along the longitudinal lines 11 may be performed to expose the tips of the optical wafers 14 for the subsequent texturing operations. The optical wafers 14 may be left connected at their bases for the subsequent texturing operation, or separated at their bases along with their tips. FIG. 2 illustrates the latter option, where the optical wafers 22 are separated at their tips and bases. The resulting series of exposed tips and exposed apertures resulting from separation and discard of the cutouts 24 outlined by oval cutout lines 23 are ready for the texturing operation. This separation operation is shown as block 54 in FIG. 5.

If the narrow strips are not already rolled up, they may be formed into a roll as shown in block 55 of FIG. 5. Alternatively, they may be stacked. FIG. 3 illustrates a roll 31 or coil of optical wafers 32. These optical wafers 32 are still joined side-to-side at the transverse lines 33, which are shown as being formed on both sides of the strips but which may be formed on only one side if desired. However, the optical wafers 32 now have projecting tips 34, which are narrowed in comparison to the width of the rectangular portion of the optical wafers, wherein the top surface of each of the tips is bare, i.e. exposed, as opposed to being clad. Coating with a cladding before performing a cutting and separation at longitudinal lines 11 (FIG. 1) results in tips 34 having an unclad area corresponding to the separation at the longitudinal lines 11. Thus the very top surface of the tip is essentially bare polymer, readily accessible for any subsequent surface texturing process. Any desired number of wafers may be in these rolls, depending upon the ease or difficulty of handling small or large diameter rolls of the wafers. Excising of these rolls from the clad sheeting may be accomplished by passing the clad sheeting through a die cutting roller assembly, but may also be done by passing through a mounted array of razor blades or through an array of shearing rollers. Registration of the lines so as to achieve proper placement of the separations may be done using techniques well known to persons of ordinary skill in the art. Alternatively or in concert, the cutout apertures may be used for locating or registering the sheeting relative to cutting blades. In particular, accurate placement of the longitudinal lines 11 (FIG. 1) is particularly desired, so that all exposed tips will be of the same cross-sectional area throughout a roll of the wafers.

The roll 31 is then passed through a texturing operation wherein the tips are subjected to a texturing treatment to provide a greatly increased surface area for deposit of an analyte-reactive reagent, so that a sufficiently strong signal may be generated in a chromatic analysis method for rapid and accurate assay. Texturing may be performed using various techniques. One suitable technique involves texturing by means of a directed beam of atomic oxygen, as set forth in U.S. Pat. No. 5,560,781 issued Oct. 1, 1996 to Banks et al., which is incorporated herein in its entirety by reference thereto. Atomic oxygen may be used to microscopically alter the surface morphology of polymeric or plastic materials in space or in ground laboratory facilities. For polymeric or plastic materials whose sole oxidation products are volatile species, directed atomic oxygen reactions produce surfaces of microscopic cones. However, isotropic atomic oxygen exposure results in polymer surfaces covered with lower aspect ratio sharp-edged craters. Isotropic atomic oxygen plasma exposure of polymers typically causes a significant decrease in water contact angle as well as altered coefficient of static friction. Atomic oxygen texturing of polymers is further disclosed and the results of atomic oxygen plasma exposure of thirty-three (33) different polymers, including typical morphology changes, effects on water contact angle, and coefficient of static friction, are presented in an article by Banks et al., "Atomic Oxygen Textured Polymers," NASA Technical Memorandum 106769, Prepared for the 1995 Spring Meeting of the Materials Research Society, San Francisco, Calif., Apr. 17-21, 1995, which hereby is incorporated herein in its entirety by reference thereto. In this regard, organopolymeric plastics amenable to oxidation and etching by atomic oxygen are advantageous for use in the preparation of sensors based on the optical wafers described herein, such plastics also needing to display good transparency characteristics toward light frequencies intended to be used in subsequent sensors. Some examples of such plastics include poly(methyl methacrylate), polystyrene, styrene-acrylonitrile copolymer, various methyl methacrylate copolymers, and polycarbonate.

FIG. 4 illustrates a single optical wafer prepared in accordance with the methods described here. Most of the optical wafer 41 is a generally rectangular-shaped portion 42 which tapers into a narrowed tip 43 having a distal surface 44 whereupon a textured surface may be formed and wherein a deposit of an analyte-reactive reagent may be made.

These optical wafers may have thicknesses in the range of 1 micrometer ($\mu$m) to 10,000 $\mu$m, preferably in the range of 10 $\mu$m to 1000 $\mu$m, and more preferably in the range of 200 $\mu$m to 700 $\mu$m. Polymeric films or sheeting having thicknesses in the range of 276 $\mu$m to 552 $\mu$m are particularly preferred. The length of the optical wafer is conveniently on or about 250 mm, but may be shorter or longer, such as in the range of 50 mm to 1000 mm. In a device for blood glucose determination incorporating both a lancet and the optical wafer, the lancet customarily has a length of approximately 250 mm itself, and an optical wafer of the same approximate length is advantageous for handling, packaging and usage characteristics. The width of the tip at its exposed end may range from 0.1 mm to 10 mm, preferably 0.5 mm to 5 mm, more preferably 1 mm to 2 mm. The narrowest widths may involve additional effort to accurately cut and control, while the widest widths may present an unnecessarily large surfaces to wet out with a blood drop in the range of 0.1 $\mu$l to 0.5 $\mu$l (microliter). For particular ease in handling, the shape of the optical wafer may be generally rectangular on three sides, the fourth side being a tapered tip. The width of the body of the wafer is illustratively 2- to 100-fold the width of the tip, preferably 2.5- to 5-fold the width of the tip. A particularly preferred wafer formed in accord with this invention would have a length of approximately 250 mm, a width of approximately 4.5 mm along most of its length dimension, and a tapering to a tip, the width of the tip being approximately 1.6 mm.

Figure 6:
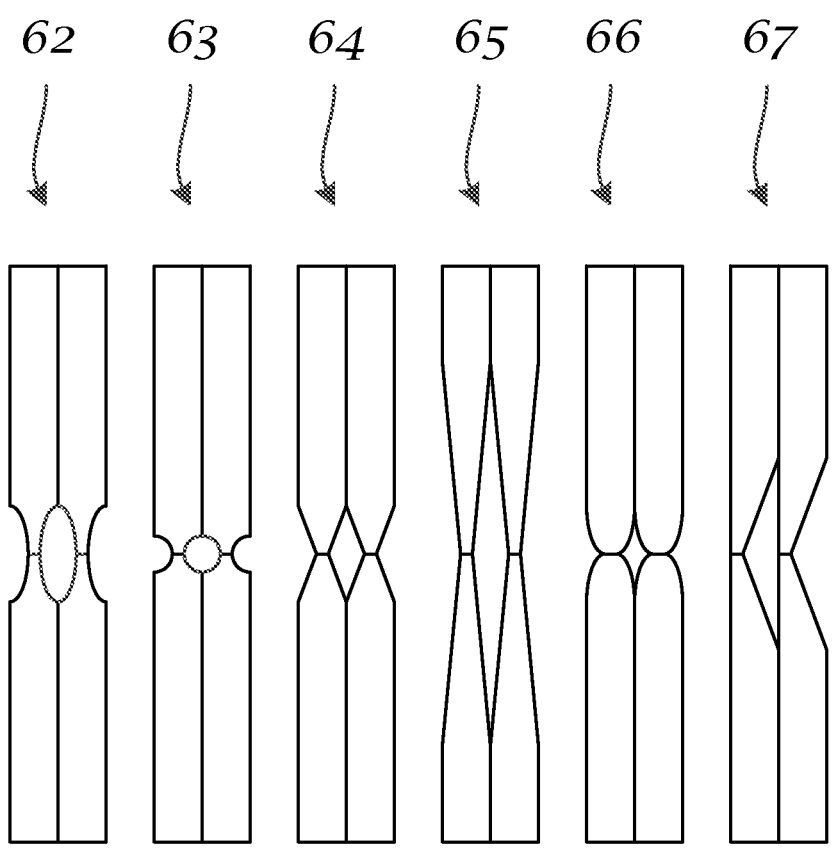
FIG. 6 is a schematic drawing of various cutouts suitable for forming the optical wafers.

FIG. 6 shows various illustrative clusters of optical wafers formed from different cutout configurations. Cluster 62 uses oval cutouts, cluster 63 uses circular cutouts, cluster 64 uses diamond cutouts, cluster 65 uses elongated diamond cutouts, and cluster 66 uses a star-like cutout. The tips of the optical wafers need not be centered and the the optical wafers need not be symmetrical, as shown in cluster 67 which uses a triangular cutout. Other cutout configurations are contemplated as well, with the choice of a particular cutout configuration being a matter of design choice both for manufacturing considerations and optical performance. For practical purposes of handling, the length of the sides of the wafers in the main portion is preferred to exceed the projecting length of the tip of the wafer, but as shown by cluster 65, this is not a requirement.

The rolls 31 are further processed in an analyte-reactive reagent deposition operation 57 (FIG. 5), which may include the deposition of hollow microspheres for enhanced sensitivity, in accordance with the aforementioned Nomura patent documents. An analyte-reactive reagent for the analyte is disposed on the tips 34 of the optical wafers 32 in optical communication therewith, and a plurality of light scattering particulate bodies may be dispersed through the analyte-reactive reagent, the particulate bodies being adapted to contribute to reflectance of light from the optical material body back into the optical material body through at least a portion of the analyte-reactive reagent, when the analyte-reactive reagent is in reaction with the analyte. In particular, use is made of hollow polymeric microspheres, which provide for significantly augmented reflectance of a light beam emitted from the optical material into the sampling zone. Further described is a device wherein exists a sampling zone associated with an analyte-reactive reagent wherein a portion of the reagent is disposed between the surface of the optical material and the hollow polymeric microspheres, the hollow polymeric microspheres providing for reflectance of a light beam emitted from the optical material into the sampling zone.

A specific and particularly advantageous implementation may be summarized as follows. A continuous roll of optically transparent sheeting, preferably based on a polymethacrylate-based polymer or copolymer, is passed through a machine roller operation wherein cutouts are excised and transverse lines are embossed into the roll of sheeting. The roll is then passed through a gas plasma apparatus wherein a fluorocarbon based coating is applied to all exposed surfaces of the sheeting to create optical cladding. The roll of clad material is then passed through a cutting operation wherein the sheeting is slit along longitudinal lines into continuous strips. These strip rolls are then placed, in roll form, in a chamber and the exposed tips are etched by means of a directed beam of atomic oxygen. The textured tips of the strip rolls are then impregnated with a fluid slurry mixture of analyte-reactive reagent and polymeric hollow microspheres (such as available as Ropaque®, a tradename of Rohm and Haas) and dried, the fluid mixture depositing the reagent and the microspheres in the crevices in the etched tips. The strip rolls are then separated into individual sensor strips and loaded into small cartridges customarily of a type used in blood glucose testing by diabetic patients.

The specific implementation is now described in greater detail, with reference to the figures where appropriate. With reference to FIG. 1, a suitable sheet of an optically transparent plastic is passed through a first step wherein oval, diamond, or other approximately similarly shaped die-cut lines 13 are formed, wherein also transverse lines 12 are embossed to a depth that will allow later separation or detachment of one wafer from another in a later step. Machine-direction die-cut lines 10, 11 are not done at this stage, but are done in a later step. The cutouts are then removed from the continuous sheet, providing essentially a perforated sheet of material. Multiple arrays of perforations are preferably positioned in the continuous sheet of material in parallel arrangements, thus providing a parallel array of "double" wafers held side to side by narrowed connecting bridges of the sheet material and flat base to flat base where the longitudinal lines 10 and 11 are not not yet effected. The perforated/cut/embossed sheet is then passed through a coating step wherein the surface is coated with a cladding of an organopolymeric material, preferably of high fluorine content. Cladding polymer may be applied by dip-coating, spraying, extrusion coating, or gas plasma coating. Applying such a coating by gas plasma polymerization is particularly suited to this intended application. The resulting continuous clad sheet is then passed through a die-cutting operation to produce strips of clad wafers, wherein tips and bases are separated from previously adjoining tips and bases on adjacent strip rolls. The tips are narrow, and their distal surfaces do not having cladding because of the exposure at the longitudinal line 11 having now been performed. The strips, which can be easily handled in roll form, are then exposed to atomic oxygen texturing applied to the exposed tip surfaces. Because of the presence of cladding material elsewhere on the sheet surfaces, including the embossed lines and the surfaces exposed earlier in the cutout step, atomic oxygen texturing is in practice naturally restricted primarily to the freshly exposed sheet material on the tip distal surfaces. Subsequent to the atomic oxygen texturing (or to other means of texturing of the exposed tip surfaces that may become applicable), the textured tip strips are treated so as to deposit an analyte-reactive reagent, preferably with reflectance-enhancing hollow polymeric beads, as disclosed in the aforementioned Nomura patent documents. The resulting optical wafer is suitable for use as an optical sensor element capable of assaying analytes such as blood glucose when contacted with a biological fluid at the tip and illumined with a light beam into the end of the wafer opposite to the tip.

A sample of blood or other body fluid is presented to a surface of the tip of the optical wafer, wherein an analyte-reactive reagent is present as a coating. The surface may be smooth, or the surface may be advantageously textured so that it presents the morphology of a field of elongated projections. The projections may be suitably spaced apart to exclude certain cellular components such as blood cells in a body fluid sample from entering into the spaces between the projections, while permitting the remaining part of the body fluid sample, which contains the analyte, to enter into those spaces.

The targeted analyte contacts an analyte-specific chemistry on the surface of the sensor, whereupon the analyte and a specific reagent interact in a manner that is optically detectable. Suitable analyte-specific chemistries may include receptor molecules as well as reactive molecules. Commonly, analyte-specific chemistries include components that generate colored species, and optical detection is based on the density and spectral nature of the colored species. In the case of blood containing cellular elements such as erythrocytes, spatial exclusion of the erythrocytes from the zone of the reagent is an important advantage of suitably textured analytical sites, when certain color development chemistries are used where the erythrocytes would interfere in such color-based assays. In commonly applied chemistries for analyzing blood sugar levels, for instance, erythrocytes often absorb light in the same general range of light frequencies in optical determinations, and must be excluded in some manner so as not to negatively influence the analytical results. The nature and arrangement of the analyte-specific chemistry varies depending on the application. For example, the analyte-specific chemistry may be a layer of one type of chemistry or an ordered array or a finely mixed composite of different types of analyte-specific chemistries. For convenience, these various options are grouped together during the remainder of this disclosure by using the term "analyte-reactive reagent". The optically detectable change may occur specifically in the coating of the analyte-reactive reagent, or in a deposit developed on the coating (such as by binding of targeted analytes), or by development of reaction products in the fluid immediately in contact with the reagent. For purposes of this disclosure, these various possibilities which each involve slightly different spatial regions are included under the term "reagent sampling zone".

A light beam of a suitable frequency or range of frequency is transmitted through the base of the optical wafer at the opposite end thereof and from there through the tip into the reagent sampling zone. Changes in the spectral nature of the light beam advantageously occur as a function of optically detectable changes in the reagent sampling zone due to interaction of the analyte-reactive reagent with an analyte in the fluid to be analyzed. When detecting the spectral changes using reflectance spectroscopy, any part of this light beam that radiates in a direction away from the optical material through which the light beam is brought to the reagent sampling zone does not generally reenter the optical material, and does not contribute to the measurement. The techniques described herein enhance the amount of this light beam that is returned to and captured within the optical material for subsequent analysis. This technique for enhanced reflectance is optimally in the form of particles that scatter light. These particles may be composed of inorganic or organic materials. Inorganic particles useful as reflectance enhancing agents include silicates and related glasses, and may be in the shape of beads or similarly spherical shapes. They may be solid or hollow. Organic particles useful as reflectance enhancing agents include natural and synthetic polymers of various compositions, and may also be solid or hollow. Hollow beads are particularly effective. So that the analyte-reactive reagent may be accessed by the fluid sample, these reflectance enhancing particles are desirably not film-forming, meaning that a coating or array of these particles does not form a film impenetrable to fluid transport. These particles are associated with an analyte-reactive reagent coating, preferably by co-deposition as a mixed coating on the surface of an optical material, so as to be present in the reagent sampling zone. In practice, the analyte-reactive reagent is present as a coating intimately in contact with a surface of the optical material, and the suitable reflectance enhancing particles are in contact with the reagent layer but optimally extend beyond the reagent layer spatially. Thus, in one configuration, a majority of the analyte-reactive reagent is advantageously sandwiched between the optical material and the reflectance enhancing particles. A particularly effective arrangement is a textured surface on an optic material wherein both the analyte-reactive reagent and the reflectance enhancing particles are deposited within valleys or crevices of the surface.

The reflectance enhancing particles are normally to be applied to the surface of an optical material from an aqueous dispersion. The particles may be co-deposited on the surface along with the analyte-reactive reagent in a single step. Alternatively, the particles may be deposited in a separate step, preferably after first depositing a coating of the reagent. Drying of the coating or coatings at some point in the process is accomplished so as to present a dry sensor for handling and storage.

Various chemistries may be employed as analyte-reactive reagents, and a variety of analytes in blood or other biological fluids may be assayed by use of the sensors made accordingly with the invention disclosed herein. For blood glucose, which is a commonly assayed analyte, a suitable reagent is described in the aforementioned Nomura U.S. Pat. No. 8,008,068 and is useful as well in the sensor described herein.

The description of the invention including its applications and advantages as set forth herein is illustrative and is not intended to limit the scope of the invention, which is set forth in the claims. Variations and modifications of the embodiments disclosed herein are possible, and practical alternatives to and equivalents of the various elements of the embodiments would be understood to those of ordinary skill in the art upon study of this patent document. Moreover, any specific values given herein are illustrative, and may be varied as desired. These and other variations and modifications of the embodiments disclosed herein, including of the alternatives and equivalents of the various elements of the embodiments, may be made without departing from the scope and spirit of the invention, including the invention as set forth in the following claims.

The invention claimed is:

1. An optical wafer for use in manufacturing an optical sensor element, comprising:
   a flat optically transparent body elongated in a longitudinal direction and tapering down at one end to a tip, the tip being transverse to the longitudinal direction and presenting a textured field of elongated projections; and
   an analyte-reactive reagent disposed on the tip;
   wherein the flat optically transparent body has two parallel major surfaces and an edge contiguous to the major surfaces, the tip being a portion of the edge, a further portion of the edge being a base transverse to the longitudinal direction, and further portions of the edge being two sides respectively extending between the base and the tip generally in the longitudinal direction; the major surfaces being coated with cladding; and each of the sides being partially coated with cladding toward the base and being fully coated with cladding toward the tip; and
   wherein each of the sides toward the base comprises a ridge of unclad optically transparent body material, flanked by respective coterminous lengths of cladded optically transparent body material.

2. The optical wafer of claim 1 further comprising a plurality of particulate bodies dispersed through the analyte-reactive reagent, the particulate bodies being adapted to contribute to reflectance of light.

3. The optical wafer of claim 2 wherein the particulate bodies comprise hollow polymeric spheres transparent to visible light.

4. The optical wafer of claim 1 wherein the optically transparent body is generally rectangular in shape.

* * * * *